United States Patent
Samaniego et al.

(10) Patent No.: US 10,772,986 B2
(45) Date of Patent: Sep. 15, 2020

(54) FASCIA FIBROUS COMPOSITIONS AND METHODS FOR THEIR USE AND MANUFACTURE

(71) Applicant: AlloSource, Centennial, CO (US)

(72) Inventors: Adrian C. Samaniego, Centennial, CO (US); Teresa C. Romansky, Denver, CO (US); Matthew J. Southard, Denver, CO (US)

(73) Assignee: AlloSource, Centennial, CO (US)

( * ) Notice: Subject to any disclaimer, the term of this patent is extended or adjusted under 35 U.S.C. 154(b) by 327 days.

(21) Appl. No.: 15/876,809

(22) Filed: Jan. 22, 2018

(65) Prior Publication Data
US 2018/0207314 A1    Jul. 26, 2018

Related U.S. Application Data

(60) Provisional application No. 62/450,957, filed on Jan. 26, 2017.

(51) Int. Cl.
*A61L 17/08* (2006.01)
*A61L 17/12* (2006.01)
(Continued)

(52) U.S. Cl.
CPC ........ *A61L 17/08* (2013.01); *A61B 17/06166* (2013.01); *A61L 17/10* (2013.01);
(Continued)

(58) Field of Classification Search
CPC ...... A61B 17/06166–2017/0619; A61L 17/08; A61F 2/06
See application file for complete search history.

(56) References Cited

U.S. PATENT DOCUMENTS 2,591,063 A * 4/1952 Goldberg ......... A61B 17/06166
606/231
4,361,552 A    11/1982 Baur
(Continued)

FOREIGN PATENT DOCUMENTS

WO    2007144389 A1    12/2007
WO    2011072393 A1    6/2011
(Continued)

OTHER PUBLICATIONS

Extended European Search Report for European Patent Application No. 14778466.4, dated Sep. 28, 2016, all pages.
(Continued)

*Primary Examiner* — Katrina M Stransky
*Assistant Examiner* — Brigid K Byrd
(74) *Attorney, Agent, or Firm* — Kilpatrick Townsend & Stockton LLP (57) ABSTRACT

Embodiments of the present technology may permit for native, intact, natural, human-derived, or allograft-derived fibers to be used as threads for suturing. Embodiments may include a thread for suturing. The thread may include a first portion, which includes a fascia fiber. The first portion may have a first end that includes the fascia fiber. The thread may also include a second portion including a non-human-derived fiber. The second portion may have a first end that includes the non-human-derived fiber. The first end of the second portion may be attached to the first end of the first portion. Embodiments may include a method of forming a thread. The method may include attaching a first end of a fascia fiber to a first end of a first non-human-derived fiber. The method may also include attaching a second end of the fascia fiber to a first end of a second non-human-derived fiber.

24 Claims, 7 Drawing Sheets

(51) Int. Cl.
   *A61B 17/06*      (2006.01)
   *A61B 17/00*      (2006.01)
   *A61L 17/10*      (2006.01)

(52) U.S. Cl.
   CPC ............ *A61L 17/105* (2013.01); *A61L 17/12* (2013.01); *A61B 17/06004* (2013.01); *A61B 2017/00004* (2013.01); *A61B 2017/00526* (2013.01); *A61B 2017/00964* (2013.01)

(56) References Cited

U.S. PATENT DOCUMENTS

| | | | |
|---|---|---|---|
| 4,894,063 A * | 1/1990 | Nashef | A61F 2/0077 623/13.17 |
| 5,336,616 A | 8/1994 | Livesey et al. | |
| 5,556,379 A | 9/1996 | Wolfinbarger | |
| 5,723,010 A | 3/1998 | Yui et al. | |
| 5,797,871 A | 8/1998 | Wolfinbarger | |
| 5,820,581 A | 10/1998 | Wolfinbarger | |
| 5,837,278 A | 11/1998 | Geistlich et al. | |
| 5,876,451 A | 3/1999 | Yui et al. | |
| 5,976,104 A | 11/1999 | Wolfinbarger | |
| 5,977,034 A | 11/1999 | Wolfinbarger | |
| 5,977,432 A | 11/1999 | Wolfinbarger | |
| 5,989,498 A | 11/1999 | Odland | |
| 6,024,735 A | 2/2000 | Wolfinbarger | |
| 6,152,142 A | 11/2000 | Tseng | |
| 6,189,537 B1 | 2/2001 | Wolfinbarger | |
| 6,305,379 B1 | 10/2001 | Wolfinbarger | |
| 6,326,019 B1 | 12/2001 | Tseng | |
| 6,432,710 B1 | 8/2002 | Boss | |
| 6,752,834 B2 | 6/2004 | Geistlich et al. | |
| 6,837,907 B2 | 1/2005 | Wolfinbarger | |
| 7,153,518 B2 | 12/2006 | Wironen et al. | |
| 7,347,876 B2 | 3/2008 | Tsai | |
| 7,393,437 B2 | 7/2008 | Chan | |
| 7,494,802 B2 | 2/2009 | Tseng | |
| 7,723,108 B2 | 5/2010 | Truncale et al. | |
| 7,727,550 B2 | 6/2010 | Siegal et al. | |
| 7,824,671 B2 | 11/2010 | Binder | |
| 7,875,063 B1 * | 1/2011 | Sander | A61B 17/06 264/260 |
| 7,902,145 B2 | 3/2011 | Chu | |
| 7,981,022 B2 | 7/2011 | Gellman et al. | |
| 8,021,692 B2 | 9/2011 | Hiles | |
| 8,058,066 B2 | 11/2011 | Marshall | |
| 8,071,135 B2 | 12/2011 | Liu et al. | |
| 8,105,634 B2 | 1/2012 | Liu et al. | |
| 8,153,162 B2 | 4/2012 | Tseng | |
| 8,158,141 B2 | 4/2012 | Chen | |
| 8,158,379 B2 | 4/2012 | Ronholdt | |
| 8,168,215 B2 | 5/2012 | Dufrane et al. | |
| 8,182,840 B2 | 5/2012 | Tseng | |
| 8,182,841 B2 | 5/2012 | Tseng | |
| 8,187,639 B2 | 5/2012 | Tseng | |
| 8,198,245 B2 | 6/2012 | Niklason | |
| 8,231,908 B2 | 7/2012 | Kinoshita | |
| 8,309,106 B2 | 11/2012 | Masinaei et al. | |
| 8,323,701 B2 | 12/2012 | Daniel et al. | |
| 8,357,402 B2 | 1/2013 | Ingram et al. | |
| 8,357,403 B2 | 1/2013 | Daniel et al. | |
| 8,372,437 B2 | 2/2013 | Daniel | |
| 8,372,438 B2 | 2/2013 | Daniel et al. | |
| 8,372,439 B2 | 2/2013 | Daniel et al. | |
| 8,409,626 B2 | 4/2013 | Daniel | |
| 8,420,126 B2 | 4/2013 | Tseng | |
| 8,440,235 B2 | 5/2013 | Tseng | |
| 8,455,009 B2 | 6/2013 | Tseng et al. | |
| 8,460,714 B2 | 6/2013 | Tseng et al. | |
| 8,642,092 B2 | 2/2014 | Daniel et al. | |
| 8,703,206 B2 | 4/2014 | Daniel et al. | |
| 8,703,207 B2 | 4/2014 | Daniel et al. | |
| 8,709,493 B2 | 4/2014 | Daniel et al. | |
| 8,709,494 B2 | 4/2014 | Daniel | |
| 8,822,415 B2 | 9/2014 | Trumpower et al. | |
| 8,834,928 B1 | 9/2014 | Truncale et al. | |
| 8,883,210 B1 | 11/2014 | Truncale et al. | |
| 9,265,800 B2 | 2/2016 | Daniel | |
| 9,265,801 B2 | 2/2016 | Daniel | |
| 9,272,003 B2 | 3/2016 | Daniel et al. | |
| 9,272,005 B2 | 3/2016 | Daniel | |
| 9,446,077 B2 | 9/2016 | Southard et al. | |
| 2004/0048796 A1 | 3/2004 | Hariri | |
| 2004/0267362 A1 * | 12/2004 | Hwang | A61F 2/08 623/13.15 |
| 2005/0019865 A1 | 1/2005 | Kihm | |
| 2005/0058631 A1 | 3/2005 | Kihm | |
| 2006/0234376 A1 | 10/2006 | Mistry | |
| 2007/0160588 A1 | 7/2007 | Kihm | |
| 2008/0046095 A1 | 2/2008 | Daniel | |
| 2009/0054911 A1 * | 2/2009 | Mueller | A61B 17/0401 606/139 |
| 2009/0248070 A1 * | 10/2009 | Kosa | A61B 17/06166 606/232 |
| 2009/0258082 A1 | 10/2009 | Nikaido et al. | |
| 2010/0112543 A1 | 5/2010 | Ngo | |
| 2010/0124776 A1 | 5/2010 | Shi | |
| 2010/0196478 A1 | 8/2010 | Masters | |
| 2010/0304487 A1 | 12/2010 | Truncale | |
| 2011/0091434 A1 | 4/2011 | Miller | |
| 2011/0104100 A1 | 5/2011 | Riordan | |
| 2011/0160857 A1 | 6/2011 | Bracone | |
| 2011/0206776 A1 | 8/2011 | Tom et al. | |
| 2011/0256202 A1 | 10/2011 | Tom et al. | |
| 2011/0262393 A1 | 10/2011 | Yang | |
| 2012/0009644 A1 | 1/2012 | Hanby et al. | |
| 2012/0009679 A1 | 1/2012 | Hanby et al. | |
| 2012/0010725 A1 | 1/2012 | Hanby et al. | |
| 2012/0063997 A1 | 3/2012 | Hunter | |
| 2012/0078378 A1 | 3/2012 | Daniel et al. | |
| 2012/0083900 A1 | 4/2012 | Samaniego et al. | |
| 2012/0109193 A1 * | 5/2012 | Primavera | A61B 17/06166 606/228 |
| 2012/0141595 A1 | 6/2012 | Tseng et al. | |
| 2012/0142102 A1 | 6/2012 | Chen | |
| 2012/0164114 A1 | 6/2012 | Abbot | |
| 2012/0189583 A1 | 7/2012 | Liu et al. | |
| 2012/0189586 A1 | 7/2012 | Harrell | |
| 2012/0191184 A1 | 7/2012 | Chen | |
| 2012/0201787 A1 | 8/2012 | Abbot | |
| 2012/0225484 A1 | 9/2012 | Bhatia et al. | |
| 2012/0269774 A1 | 10/2012 | Ichim | |
| 2012/0276080 A1 | 11/2012 | Kinoshita et al. | |
| 2012/0276150 A1 | 11/2012 | Lauritzen et al. | |
| 2012/0294810 A1 | 11/2012 | Daniel | |
| 2012/0294811 A1 | 11/2012 | Daniel | |
| 2012/0294908 A1 | 11/2012 | Daniel et al. | |
| 2012/0294910 A1 | 11/2012 | Daniel et al. | |
| 2012/0310367 A1 | 12/2012 | Connor | |
| 2012/0328690 A1 | 12/2012 | Tseng et al. | |
| 2013/0004465 A1 | 1/2013 | Aberman | |
| 2013/0006385 A1 | 1/2013 | Daniel | |
| 2013/0052169 A1 | 2/2013 | Marom | |
| 2013/0202676 A1 | 8/2013 | Koob et al. | |
| 2013/0211523 A1 | 8/2013 | Southard et al. | |
| 2013/0218274 A1 | 8/2013 | Spencer et al. | |
| 2013/0230561 A1 | 9/2013 | Daniel et al. | |
| 2013/0344162 A1 | 12/2013 | Morse et al. | |
| 2014/0017280 A1 | 1/2014 | Daniel et al. | |
| 2014/0050788 A1 | 2/2014 | Daniel et al. | |
| 2014/0052247 A1 | 2/2014 | Daniel et al. | |
| 2014/0052274 A1 | 2/2014 | Koob et al. | |
| 2014/0106447 A1 | 4/2014 | Brown et al. | |
| 2014/0140964 A1 | 5/2014 | Brown et al. | |
| 2014/0205646 A1 | 7/2014 | Morse et al. | |
| 2014/0214176 A1 | 7/2014 | Daniel et al. | |
| 2014/0234387 A1 | 8/2014 | Daniel et al. | |
| 2014/0255496 A1 | 9/2014 | Daniel et al. | |
| 2014/0255508 A1 | 9/2014 | Morse et al. | |
| 2014/0271790 A1 * | 9/2014 | Southard | A61K 35/35 424/443 |

(56) References Cited

U.S. PATENT DOCUMENTS

2015/0140114 A1    5/2015  Sasko
2017/0055983 A1*   3/2017  Bracy .............. A61B 17/06166

FOREIGN PATENT DOCUMENTS

| WO | 2012083021 A1 | 6/2012 |
| WO | 2012083023 A1 | 6/2012 |
| WO | 2012088396 A2 | 6/2012 |
| WO | 2012095316 A1 | 7/2012 |
| WO | 2012112410    | 8/2012 |
| WO | 2012112417    | 8/2012 |
| WO | 2012112441    | 8/2012 |
| WO | 2012116372 A1 | 8/2012 |
| WO | 2012136701 A1 | 10/2012 |
| WO | 2012170905 A1 | 12/2012 |
| WO | 2013032938 A1 | 3/2013 |

OTHER PUBLICATIONS

International Search Report and Written Opinion for PCT/US2014/023737, dated Jul. 14, 2014, 12 pages.

* cited by examiner

FASCIA FIBROUS COMPOSITIONS AND METHODS FOR THEIR USE AND MANUFACTURE

CROSS-REFERENCES TO RELATED APPLICATIONS

This application claims the benefit of priority to U.S. Provisional Application No. 62/450,957, filed Jan. 26, 2017, the entire contents of which are incorporated herein by reference for all purposes.

BACKGROUND

Embodiments of the present invention relate generally to the field of allogeneic transplants, and in particular to allograft compositions containing fascia, fat, or dermis tissue, and methods for their use and manufacture.

Human tissue compositions, which may be derived from cadaveric donors, have been used for many years in various surgical procedures. Allograft and autograft tissue are both derived from humans; the difference is that allograft is recovered from an individual (e.g. donor) other than the one (e.g. patient) receiving the graft. Allograft tissue is often taken from cadavers that have donated their bodies so their tissue can be used for living people who are in need of it, for example, patients who are undergoing surgery for various reasons. Such tissues represent a gift from the donor or the donor family to enhance the quality of life for other people.

Although human tissue compositions and methods are presently available and provide real benefits to patients in need thereof, many advances may still be made to provide improved compositions and methods for for their use and manufacture. The fibrous fascia compositions and treatment and manufacture methods described herein provide further solutions and answers to at least some of these outstanding needs.

BRIEF SUMMARY

Embodiments of the present technology may permit for native, intact, natural, human-derived, or allograft-derived fibers to be used as threads for suturing. In addition, embodiments may avoid synthetic components, such as synthetic fibers, non-allograft-derived fibers, non-human-derived fibers, or glue, being left in contact with or in a patient. Embodiments may allow for reduced, minimal, or no possibility of an immunoresponse related to suture threads. Suture threads disclosed herein may also result in greater utilization of the gifts provided by donors, thereby increasing the value and reach of donations. Greater utilization of intact fibers also may result in economic benefits. Embodiments of the present invention encompass techniques for processing fascia fibers or filaments into surgical products, and administering such products to recipient patients. Embodiments of the present invention include fascia fibers used for suturing.

Fascia tissue includes layers of fibrous material within the body that surround muscles and other anatomical features. For example, an abundance of fascia connective tissue can be found at the quadriceps and inner or frontal thigh areas. Typically, fascia is flexible and contains collagen fibers that have been formed by fibroblasts.

In a first aspect, embodiments may include a thread for suturing. The thread may include a first portion, which includes a fascia fiber. The first portion may have a first end that includes the fascia fiber. The thread may also include a second portion including a non-human-derived fiber. The second portion may have a first end that includes the non-human-derived fiber. The first end of the second portion may be attached to the first end of the first portion.

In a second aspect, embodiments may include a method of forming a thread. The method may include attaching a first end of a fascia fiber to a first end of a first non-human-derived fiber. The method may also include attaching a second end of the fascia fiber to a first end of a second non-human-derived fiber.

In a third aspect, embodiments may include a method of suturing. The method may include inserting a thread into a soft tissue. The thread may include a first portion that includes a fascia fiber and a second portion that includes a non-human-derived fiber. Inserting the thread into the soft tissue may include inserting the second portion into the soft tissue before the first portion. The method may also include removing the second portion from the first portion when the first portion is in contact with the soft tissue.

DETAILED DESCRIPTION

Embodiments of the present invention include threads for suturing, and methods of forming and using the threads. The threads may include a human-derived fiber portion and a non-human-derived portion. Human-derived fibers may also be referred to as natural or native fibers. Human-derived fibers may include allograft-derived fibers and may specifically include fascia fibers. In this application, non-human-derived may refer to fibers or other material that may not be native to a donor or a subject of suturing. Non-human-derived fibers may also be referred to as synthetic fibers or non-native fibers. For example, if a human patient is to be sutured, a fiber such as silk may be considered synthetic. The combination of a donor fascia fiber portion with one or more non-human-derived portions may allow for greater utilization of donor fascia fibers and a lower likelihood of an untoward immunoresponse when the thread is placed in a recipient or patient. The decreased likelihood of an immune-related rejection response is at least partly because of the absence of donor-derived blood elements. These potentially immunogenic ingredients may be removed by the methods described herein, which then render the fibers acellular and non-immunogenic. Embodiments of the present technology also may benefit from clinical and therapeutic advantages of using fascia fiber for suturing since the fascia fiber as a human-derived collagenous material is biocompatible with human recipient tissue and unlikely to provoke a biological foreign body response.

Conventional techniques of suturing have drawbacks. Such methods presently use only non-human-derived threads. Using only non-human-derived threads introduces a non-native, normally foreign component to the patient's body. In some cases, non-human-derived threads may induce an immunoresponse or a hypoallergenic response. Non-human-derived threads also may not degrade or be remodeled in the body and may need to be removed, which may require an additional procedure.

Native fibers, such as fascia fibers obtained from a human donor, can have their own problems when substituted for non-human-derived fibers in conventional techniques. The length of fascia fibers that can be used for suturing may be limited by the length of the fascia fiber obtained from the donor body. In many cases, this length may be too short to securely suture a wound or surgical incision of a patient. The fascia fibers cannot be easily lengthened by attaching fascia fibers to other fascia fibers, with such attachments often resulting in a thread with lower strength. For example, when combining multiple fascia fibers to make the fascia portion longer without adding a binder, the fibers slide off each other once wet with forces of less than 1 lb. In addition, for a given diameter, a weave of multiple fibers has less overall strength than a straight fascia fiber. Moreover, long fascia fibers may not be uniform in thickness and in strength across the entire length of the fiber, and as a result, shorter fascia fibers may be used to maintain a minimum uniformity and strength. Even if a fascia fiber was long enough and uniform enough for a suture, suturing may often result in cutting off and discarding excess donor fascia fiber. Wasting fascia fiber is not economical and also does not properly honor the gift provided by a donor. Additionally, medical professionals, including surgeons, may be accustomed to non-human-derived fibers for suturing. Using only a fascia fiber, even if long enough for a suture, may have a different feel and resistance than a non-human-derived fiber.

The fascia may refer to a fibrous membrane which covers most major muscles, nerves, and organs. Embodiments of the present invention encompass cadaveric fascia graft compositions, and methods for their use and manufacture. For example, fascia tissue can provide a biologically-derived fibrous source of collagen that can be further manufactured or processed into predetermined various configurations, such as fascia fiber, fascia collagen bundles, fascia wires, fascia sheets, fascia filaments, and the like.

I. Threads

Figure 1A:
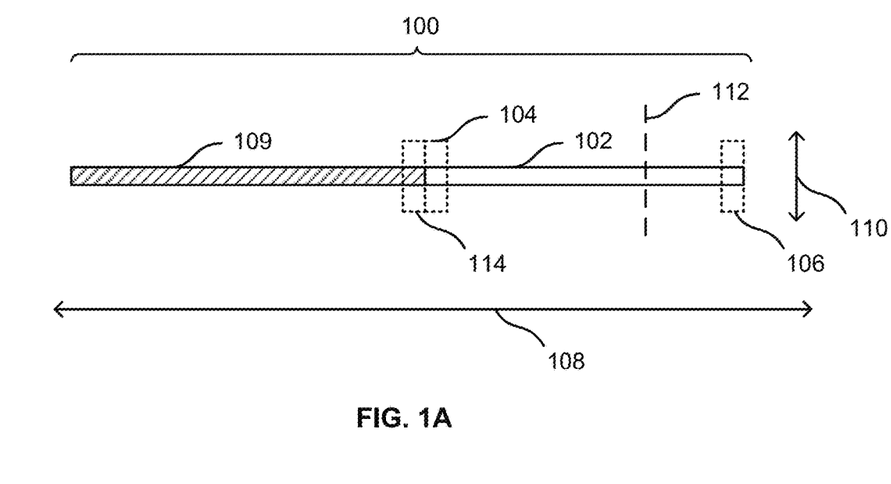
FIGS. 1A, 1B, and 1C show threads according to embodiments of the present invention.
Figure 1B:
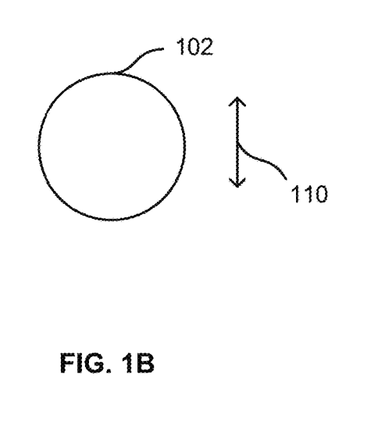

Embodiments may include a thread for suturing. The thread may include a fascia fiber attached at both ends to two non-human-derived fibers. The thread may have a strength that allows the thread to be used a surgical suture. A thread with a diameter of about 200 to 300 microns may have a strength to withstand about 5 to 7 lbs of force on average. FIG. 1A shows an example of a thread 100. Thread 100 includes a first portion 102 that includes a fascia fiber. First portion 102 may have a first end 104 that includes the fascia fiber. First portion 102 may have a second end 106 that includes the fascia fiber. The first end and the second end may be on opposite ends of the first portion. If the fascia fiber can be considered a cylinder or a solid similar to a cylinder, first end 104 and the second end 106 may include the circular or near-circular sections of the cylinder. In other words, first end 104 and second end 106 may include the surfaces at the limits of first portion 102 in either axial direction. The axial direction is illustrated by line 108. The radial direction is depicted by line 110. FIG. 1B shows a circular cross section of the thread at dashed line 112. The cross section in FIG. 1B is of first portion 102, but other portions of thread 100 may also have a circular cross section. In some instances or areas, the thread may not be perfectly circular. The radius of the thread may differ by a maximum of 5%, 10%, or 15% from the average radius. The fascia fiber may be recovered from a single cadaveric donor. The fascia fiber may include a plurality of individual fascia fiber filaments. Each fascia fiber filament may have a diameter as low as 5 µm with a length of 7 to 10 inches. Fascia fibers may be any fibers described in U.S. Patent Application No. 61/779,269 filed Mar. 13, 2013 or Ser. No. 14/204,346 filed Mar. 11, 2014, the contents of which are incorporated herein by reference for all purposes. In addition to fascia fiber, human-derived fiber may include fibers made from ligaments, tendons, or bones.

Thread 100 may also include a second portion 109 that includes a first non-human-derived fiber. Second portion 109 may have a first end 114 that includes the first synthetic fiber. The first non-human-derived fiber may include nylon, polyester, polyethylene, polyglycolic acid, polylactic acid, polyvinylidene fluoride, polypropylene, catgut, or silk. If the first non-human-derived fiber is cylindrical or near-cylindrical in shape, first end 114 may include a circular section of the first non-human-derived fiber. In other words, first end 114 may include the surface at the limit of second portion 109 in an axial direction. First end 114 of second portion 109 may be attached to first end 104 of first portion 102. First end 114 of second portion 109 may be attached to first end 104 of first portion 102 by an adhesive, which may include cyanoacrylate or a cyanoacrylate ester. The adhesive may include Dermabond® or Super Glue®. In some embodiments, second portion 109 may be melted onto first portion 102. In other embodiments second portion 109 may be stapled onto first portion 102. First end 114 of second portion 109 may be attached to first end 104 of first portion 102 directly at the end surface of each portion. In other embodiments, first end 114 of second portion 109 may be attached to first end 104 of first portion 102 because second portion 109 and first portion 102 overlap in the axial direction and the two portions are attached in the overlap.

Figure 1C:
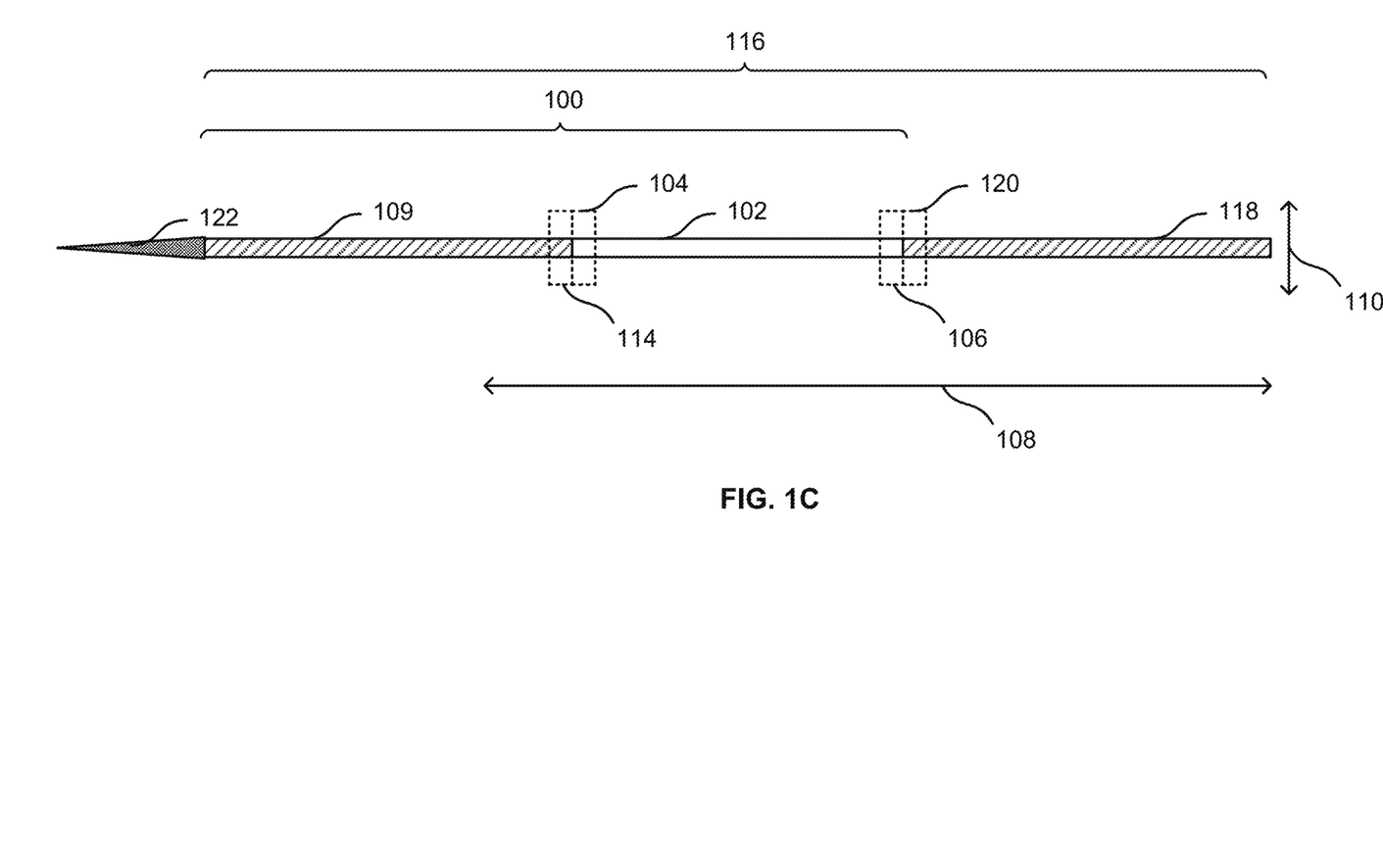

Some embodiments may include thread 116 shown in FIG. 1C. Thread 116 may include thread 100 from FIG. 1A and may further include a third portion 118 that includes a second non-human-derived fiber. Third portion 118 may have a first end 120 that includes the second non-human-derived fiber. First end 120 of third portion 118 may be similar to first end 114 of second portion 109. First end 120 may include a circular area of a cylindrical or near-cylindrical third portion 118. In some examples, first end 120 may include a surface at the limit of third portion 118 in the axial direction. First end 120 of third portion 118 may be attached to second end 106 of first portion 102. First end 120 of third portion 118 may be attached to second end 106 of first portion 102 by an adhesive, including any adhesive disclosed herein. The orientation of the attachment may be the same as any way the second portion 109 could be attached to first portion 102. The first non-human-derived fiber may be the same type of fiber as the second non-human-derived fiber. In other embodiments, the first non-human-derived fiber may be different from the second non-human-derived fiber. The second non-human-derived fiber may be added to provide a longer length to the thread. The thread may be used for orthoscopic applications. The thread may often involve tying knots on the outside of the wound or the human body, and a longer thread may allow for knots to be more easily tied and manipulated.

Thread 116 may have 4 to 8 lbs of ultimate tensile strength. The strength of the thread may be limited by the fascia fiber and may be related to the diameter of the fascia fiber. When force is applied, the thread may break at the fascia fiber and not the junction of the fascia fiber with the non-human-derived fiber. In other words, the adhesive may have a higher ultimate tensile strength than the fascia fiber.

Second portion 109 of thread 100 may contact a piercing element 122. Piercing element 122 may be a surgical needle, other needle, or any suitable device. Second portion 109 may be fastened to piercing element 122. In embodiments, one end of piercing element 122 may be crimped onto second portion 109, an adhesive may attach piercing element 122 to second portion 109, second portion 109 may be tied onto piercing element 122, or second portion 109 may be attached to piercing element 122 by other fastening means. Piercing element 122 may not be considered part of thread 100.

Thread 116 may have a length based on the intended medical or surgical procedure. The thread may be long enough so that a knot may be tied, and a medical professional may not need to use magnifying glasses tie the knot. The total length of thread 116 may be from 18 inches to 54 inches, 15 inches to 18 inches, 18 inches to 24 inches, 24 inches to 30 inches, 30 inches to 36 inches, 36 inches to 40 inches, 40 inches to 48 inches, 48 inches to 54 inches, over 48 inches, or any combination of ranges according to embodiments. The total length of thread 116 does not include piercing element 122.

First portion 102 may have a length from 6 inches to 8 inches, from 8 inches to 10 inches, from 10 inches to 12 inches, from 12 inches to 18 inches, over 18 inches, or any combination of ranges according to embodiments. First portion 102 may have a diameter from 300 µm to 400 µm, 250 µm to 300 µm, 300 µm to 350 µm, 350 µm to 400 µm, 400 µm to 450 µm, over 450 µm, or any combination of ranges according to embodiments. Thread 100 may have a maximum diameter that does not exceed the diameter of the first portion by greater than 10 µm, 20 µm, 30 µm, 40 µm, 50 µm, or 60 µm in embodiments. The maximum diameter of the thread may be where the first portion attaches to the second portion of third portion.

Second portion 109 may have a length from 6 inches to 8 inches, from 8 inches to 10 inches, from 10 inches to 12 inches, from 12 inches to 18 inches, 18 inches to 24 inches, over 24 inches, or any combination of ranges according to embodiments. Because second portion 109 may be non-human-derived fiber, second portion 109 may not be limited in length, and the length may be based on commercially available fibers. The length of third portion 118 may be equal to, within 5% of, within 10% of, or within 20% of the length of second portion 109.

II. Forming Threads

Figure 2:
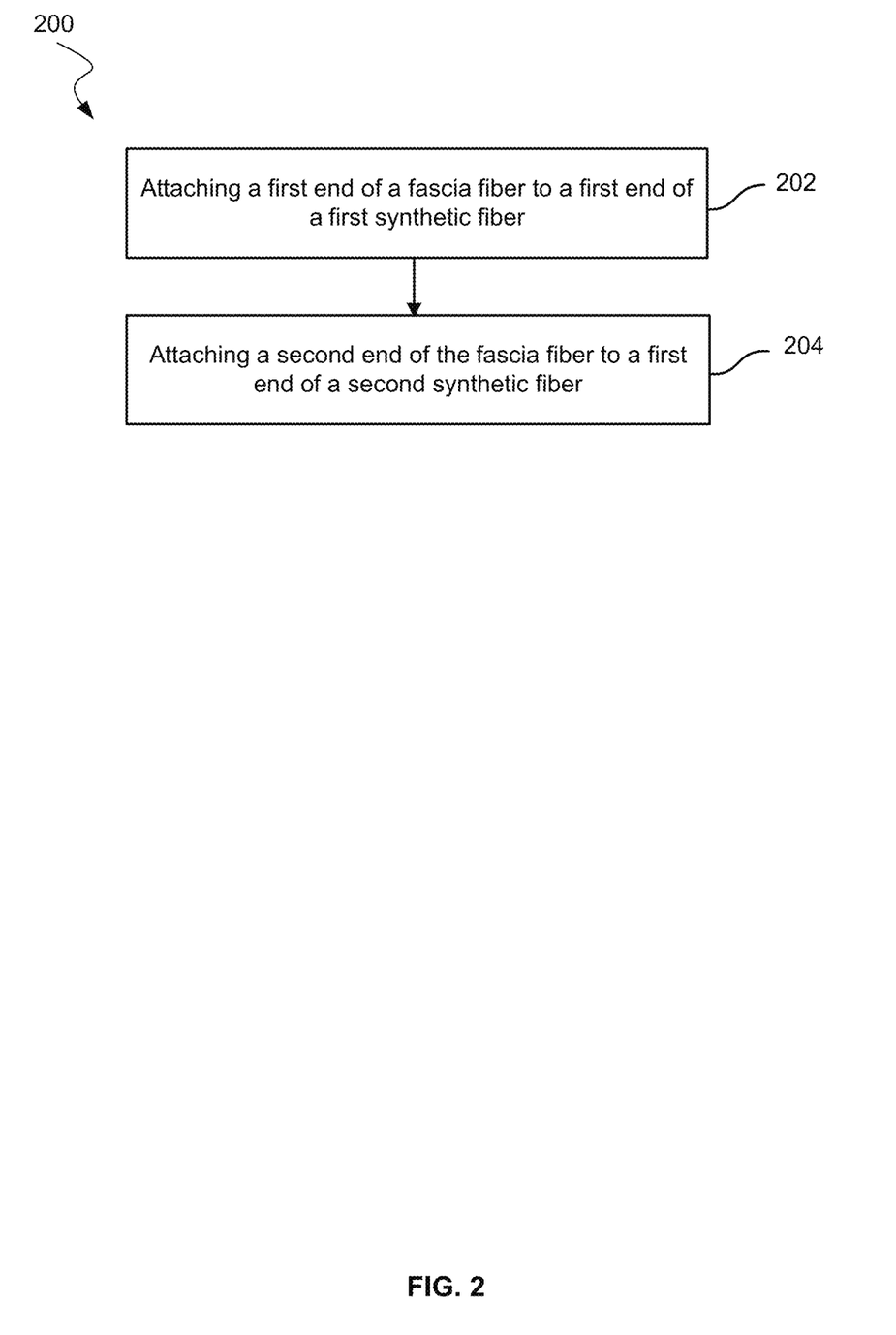
FIG. 2 shows a method of forming a thread according to embodiments of the present invention.

As shown in FIG. 2, embodiments may include a method 200 of forming a thread. The thread may be any thread described herein. Method 200 may include obtaining and forming the fascia fiber. A fascia fiber may be obtained according to U.S. patent application U.S. Patent Application No. 61/779,269 filed Mar. 13, 2013 or Ser. No. 14/204,346 filed Mar. 11, 2015, the contents of which are incorporated herein by reference for all purposes. For example, in some embodiments, a method of obtaining a fascia fiber may include obtaining a deceased donor fascia tissue, treating the deceased donor fascia tissue with acetone, and obtaining one or more intact fascia fibers from the treated deceased donor fascia tissue. An intact fascia fiber may have a diameter within a range from 5 to 200 microns. In some cases, an intact fascia fiber may have a length greater than 20 cm. The intact fascia fiber may be used directly as a fascia fiber, or the intact fascia fiber may be further processed (e.g. cut into two or more pieces) to produce a fascia fiber.

Figure 3A:
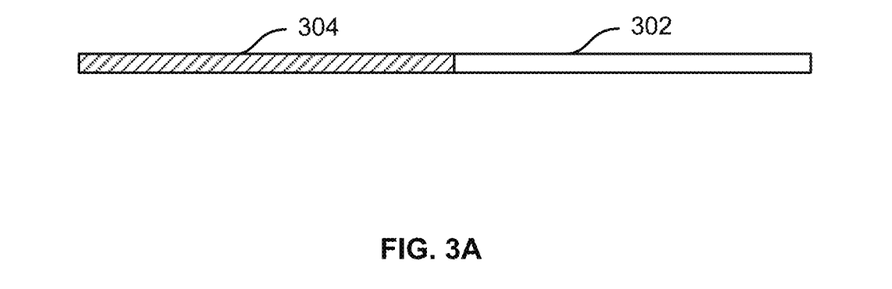
FIGS. 3A, 3B, and 3C show different attachment configurations according to embodiments of the present invention.

At block 202, method 200 may include attaching a first end of a fascia fiber to a first end of a first non-human-derived fiber. Attaching the first end of the fascia fiber to the first end of the first non-human-derived fiber may include directly binding the section at the limit of the fascia fiber in the axial direction with the section at the limit of the first non-human-derived fiber in the axial direction. For example, FIG. 3A shows an axial cross sectional view of fascia fiber 302 attached to non-human-derived fiber 304. For the insertion, non-human-derived fiber 304 may have a large diameter than fascia fiber 302 across the whole of non-human-derived fiber 304, or non-human-derived fiber 304 may have a larger diameter at only end 306.

Figure 3B:
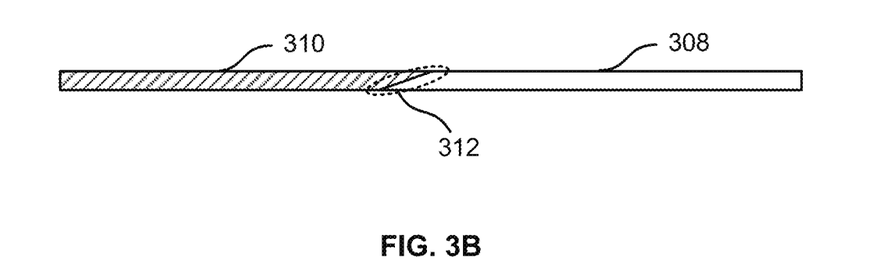

In some embodiments, method 200 may include tapering the fascia fiber to form the first end of the fascia fiber before attaching the first end of the fascia fiber to the first end of the first non-human-derived fiber. For example, FIG. 3B shows an axial cross sectional view of fascia fiber 308 and non-human-derived fiber 310. Tapering is shown in area 312. Fascia fiber 308 may be tapered at one end and from one side. Independently, non-human-derived fiber 310 may be tapered at one end and from one side. In embodiments, non-human-derived fiber 310 may not be tapered while fascia fiber may be tapered. Non-human-derived fiber 310 may be a woven fiber, which may be more difficult to taper. The tapered ends decrease the thickness of the fibers and may reduce the diameter or reduce the diameter of the thread at the junction. Avoiding increasing the diameter of the thread at the junction may be desirable for surgical applications. A smaller diameter at the junction avoids unnecessarily enlarging suture points in a patient, which may then result in faster recovery times. The first end of the fascia fiber may be attached to the first end of the first non-human-derived fiber by any adhesive described herein.

Figure 3C:
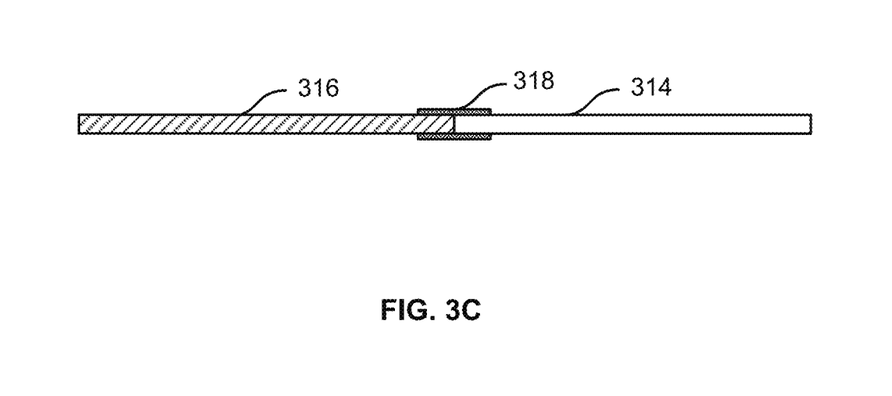

In some embodiments, method 200 may include a tubular component that may bind the fascia fiber to the non-human-derived fiber. The ends of the fibers may be inserted into the tubular component, which may be a tube, cylinder, or other similar shape. For example, FIG. 3C shows an axial cross sectional view of fascia fiber 314 and non-human-derived fiber 316. One end of fascia fiber 314 and one end of non-human-derived fiber 316 may be inserted into tube 318. Tube 318 may be reduced in size to bind the two fibers together. Before reduction in size, tube 318 may be 0.5 inches to 2 inches long, including 0.5 inches to 1 inch, 1 inch to 1.5 inches, or 1.5 inches to 2 inches. The inner diameter of tube 318 before reduction in size may be slightly larger than the diameter of the fascia fiber or the non-human-derived fiber. The thickness of the wall of tube 318 may be from 100 µm to 600 µm.

The microtube may include tubing made of acrylated olefins, polyvinylidene fluoride (e.g, Kynar®), polyvinylchloride, cellulose, polyolefins (e.g., Neoprene), polytetrafluoroethylene (e.g., Teflon®), fluoropolymer elastomer (e.g., Viton®), or other suitable material. In some embodiments, tube 318 may be heated, which may cause tube 318 to shrink and bind the fibers together. In these embodiments, tube 318 may be a material, such as those previously listed, that shrinks under application of heat. These materials are sometimes known as heat shrink tubing. Heat may be applied to the tubular component by conduction, convection, or radiation. A heat gun, heat fan (e.g., a device resembling a hair dryer), iron, heated surface, or other suitable device may be used to shrink the tubular material. Another method to reduce the size of tube 318 may be the application of a chemical that causes tube 318 to shrink. For example, cellulose tubing may shrink after water is applied. When a tubular component is used, the binding of the fibers may be solely a mechanical binding. Adhesive may be excluded to avoid difficulties or inefficiencies in applying to small fibers. However, applying an adhesive to attach fibers may be faster than using a tubular component, which requires inserting the fibers into a tubular component and then heating or otherwise treating the tubular component. In some embodiments, adhesive may be used in combination with the tubular component to additionally increase binding strength. For example, an adhesive may first be applied to two ends of fibers, and the tube may be shrunk on top of the two ends. In other embodiments, adhesive may be applied to the inner surface of the tube, and heat may be applied to shrink the tube and/or cure the adhesive. In these and other embodiments, the fascia fibers may be tapered before inserting the fascia fiber and non-human-derived fiber into a tubular component.

At block 204, method 200 may also include attaching a second end of the fascia fiber to a first end of a second non-human-derived fiber. Method 200 may include tapering the fascia fiber to form the second end of the fascia fiber before attaching the second end of the fascia fiber to the first end of the second non-human-derived fiber. Attaching the second end of the fascia fiber to the first end of the second non-human-derived fiber may be in a manner similar to any described herein for the attaching of the first end of the fascia fiber to the first end of the first non-human-derived fiber.

In some embodiments, method 200 may include determining the length of the fascia fiber to be used before attaching the fascia fiber to either non-human-derived fiber. Determining the length of the fascia fiber may include obtaining the length of a wound or surgical incision to be closed and calculating a length of the fascia fiber needed for the length of the wound or surgical incision. The length of the fascia fiber may be selected based on the length of the wound or surgical incision. The fascia fiber may be cut to the determined length. Threads may be manufactured to different lengths of fascia fiber to increase the amount of fascia fiber used and reduce the amount of fascia fiber wasted. For example, a long piece of fascia fiber may be divided into two smaller portions that may both be utilized for different applications instead of using the long piece for one application requiring a shorter fascia fiber.

In some embodiments, method 200 may include determining the length of at least one of the first non-human-derived fiber or the second non-human-derived fiber. The length of the non-human-derived fibers may be a length based on the preference of the medical professional (e.g. a surgeon who is applying thread to a patient) or a length suitable to allow the thread to be tied off.

III. Suturing

A. Methods

Figure 4:
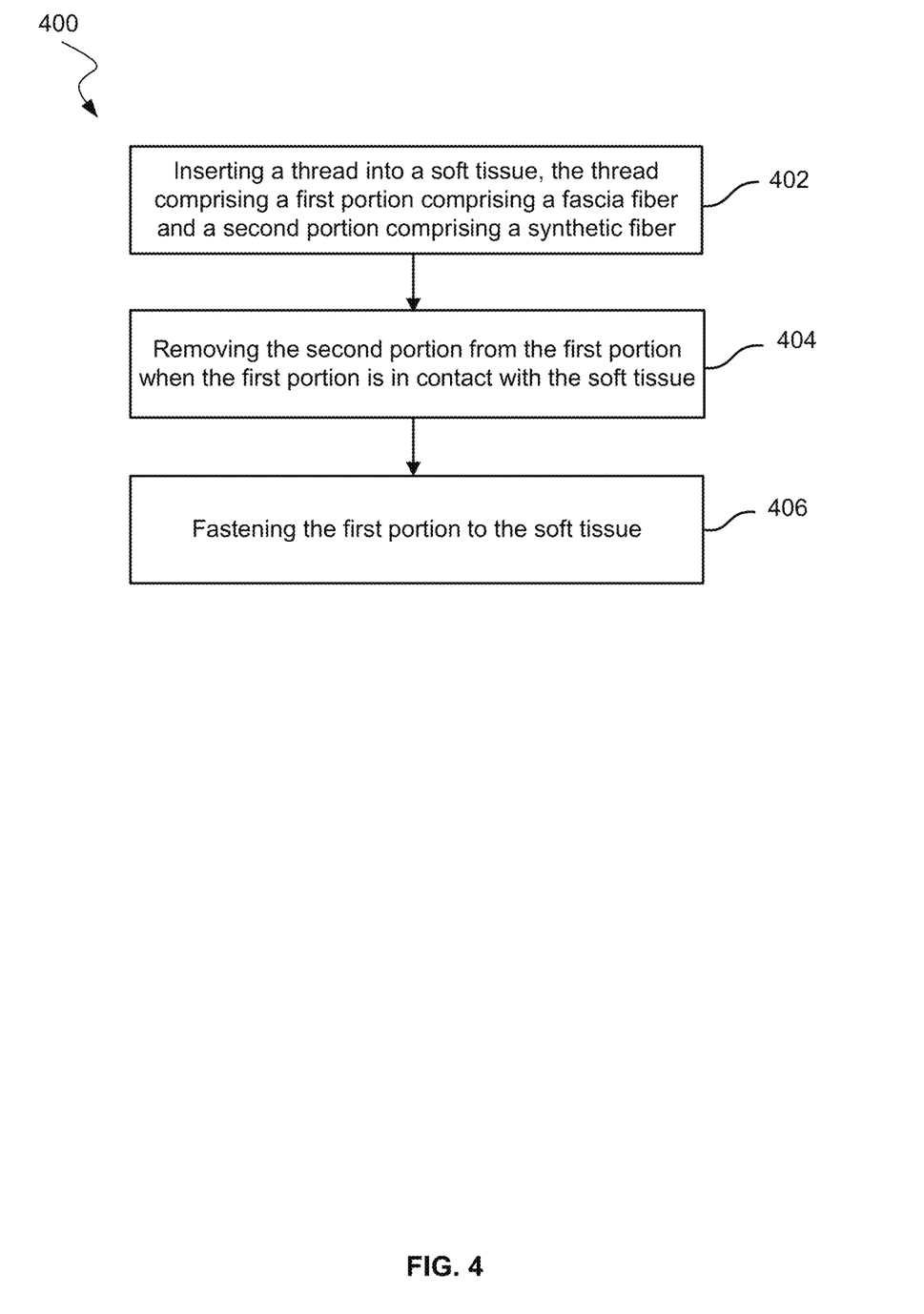
FIG. 4 shows a method of suturing according to embodiments of the present invention.

As shown in FIG. 4, embodiments may include a method 400 of suturing. Suturing may be used to close a wound or a surgical incision in a tissue of a human or animal subject.

At block 402, method 400 may include inserting a thread into a soft tissue. The soft tissue may include the skin of a human patient. The thread may include a first portion including a fascia fiber and a second portion including a non-human-derived fiber. The first portion may include any portion of the fascia fiber described herein, and the second portion may be any portion of the non-human-derived fiber described herein. Inserting the thread into the soft tissue may include inserting the second portion into the soft tissue before the first portion. Inserting the non-human-derived fiber may provide the medical professional similar tactile feedback and resistance as with conventional non-human-derived fibers for suturing. The second portion may be in contact with a piercing element. Method 400 may include attaching the second portion to the piercing element, and method 400 may include inserting the piercing element into the soft tissue before inserting the thread into the soft tissue.

Method 400 may include a thread that includes a third portion comprising a second non-human-derived fiber. The third portion may be any portion of the second non-human-derived fiber described herein. The first portion may be attached to the second portion, and the first portion may be attached to the third portion. Inserting the thread into the soft tissue, as in block 402, may exclude inserting the third portion into the soft tissue.

At block 404, method 400 may include removing the second portion from the first portion when the first portion is in contact with the soft tissue. Method 400 may also include removing the third portion from the first portion when the first portion is in contact with the soft tissue. Removing the second portion or the third portion may be by using scissors or a knife edge. Removing the portions may include removing adhesive used to attach either portion to the first portion of fascia fiber.

At block 406, method 400 may include fastening the first portion to the soft tissue. In some embodiments, fastening the first portion to the soft tissue may occur before removing the second portion from the first portion. Method 400 may include tying the first portion in a surgical knot to fasten the first portion to the soft tissue. Tying the first portion may include closing a wound or a surgical incision.

Figure 5A:
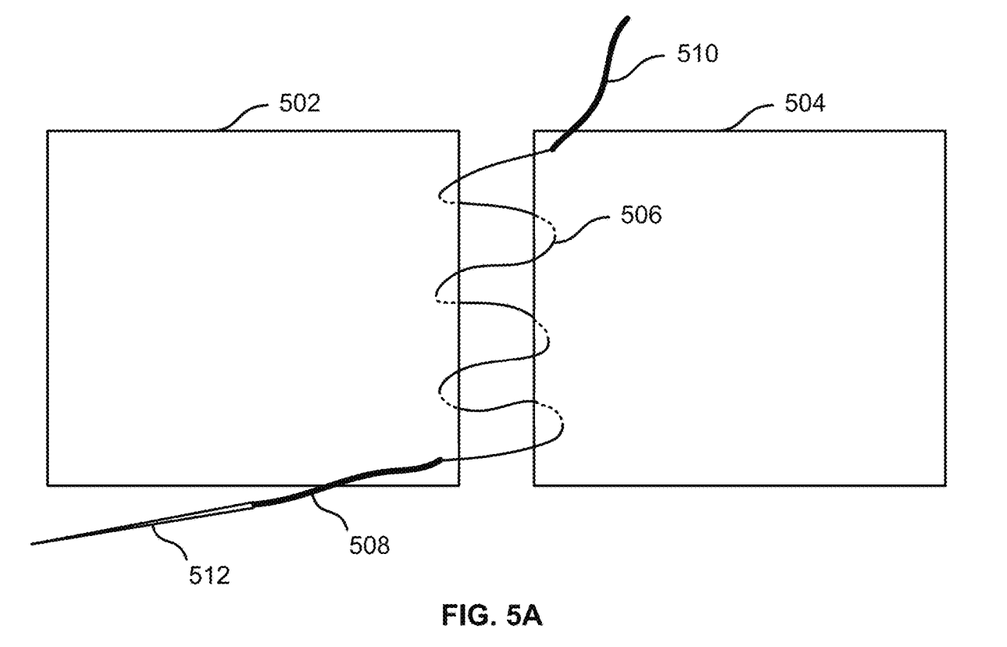
FIGS. 5A and 5B are simplified illustrations of suturing according to embodiments of the present invention.

The soft tissue may not have an immunoresponse to the first portion. The first portion may be hypoallergenic B. Example FIG. 5A is a simplified illustration of suturing. A soft tissue 502 and a soft tissue 504 are shown as being at least partially separated by some space or otherwise as being at least partially unconnected from one another. Soft tissue 502 and soft tissue 504 may be human dermal layers and may be separated by an incision, such as by a scalpel or other cutting instrument. In some examples, soft tissue 502 and soft tissue 504 may have been separated as a result of some unintended trauma to the soft tissue. Soft tissue 502 and soft tissue 504 may be connected to a common section (not shown) of soft tissue.

The thread used to suture soft tissue 502 and soft tissue 504 together may include a portion 506 of native fiber, such as fascia fiber. Portion 506 may be attached at one end to a first portion 508 of non-human-derived fiber and attached at the other end to a second portion 510 of non-human-derived fiber. First portion 508 of non-human-derived fiber may be attached to needle 512 or any other piercing element. The attachment of first portion 508 to needle 512 may be by a fastening device, or first portion 508 may be threaded through needle 512. Portion 506 may be any portion of fascia fiber described herein. First portion 508 of non-human-derived fiber and second portion 510 of non-human-derived fiber may be any portion of non-human-derived fiber described herein.

Needle 512 may pierce through soft tissue 502 and soft tissue 504 several times, drawing the thread with needle 512. In FIG. 5A, sections of portion 506 of native fiber that are behind either soft tissue 502 or soft tissue 504 are depicted as dashed lines. Suturing may include alternating piercing of soft tissue 502 and soft tissue 504. First portion 508 is completely pulled through either or both of soft tissue 502 or soft tissue 504. Second portion 510 may not enter either or both of soft tissue 502 or soft tissue 504. In other words, second portion 510 may not a cross section with its circumference surrounded by soft tissue. Second portion 510 may not contact soft tissue or may contact soft tissue only on the planar or near-planar surface of the soft tissue.

The thread may be manipulated such that portion 506 pulls soft tissue 502 and soft tissue 504 together. The effect of bringing soft tissue 502 and soft tissue 504 may be to close a wound or a surgical incision. Portion 506 of native fiber of the thread may be tied off using a surgical knot or any suitable suturing technique. First portion 508 of non-human-derived fiber and second portion 510 of non-human-derived fiber may be removed from the native fiber. Removal may be by scissors, a razor, a knife-edge, or by an applied force (e.g., pulling thread apart at the attached connection). In some cases, removal of the non-human-derived fiber may also include removal of a section of the native fiber.

Figure 5B:
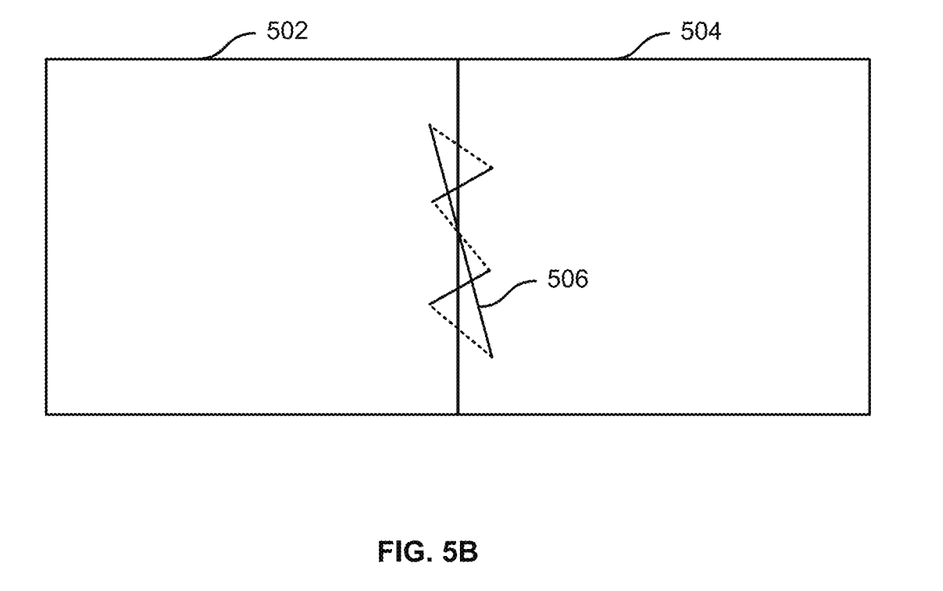

FIG. 5B illustrates a possible configuration after removal of first portion 508 and second portion 510. Soft tissue 502 and soft tissue 504 are in contact. Portion 506 of native fiber may provide a force to maintain contact between the two soft tissues. Areas where portion 506 are behind the soft tissue are illustrated as dashed lines. Because the native fiber is completely natural, the likelihood of the soft tissue suffering an immunoresponse is low. Human-derived fibers may be absorbed or remodeled (i.e., bio-resorbed and replaced by the patient's own tissue) in the human body.

IV. EXAMPLES

A. Example 1

Figure 6:
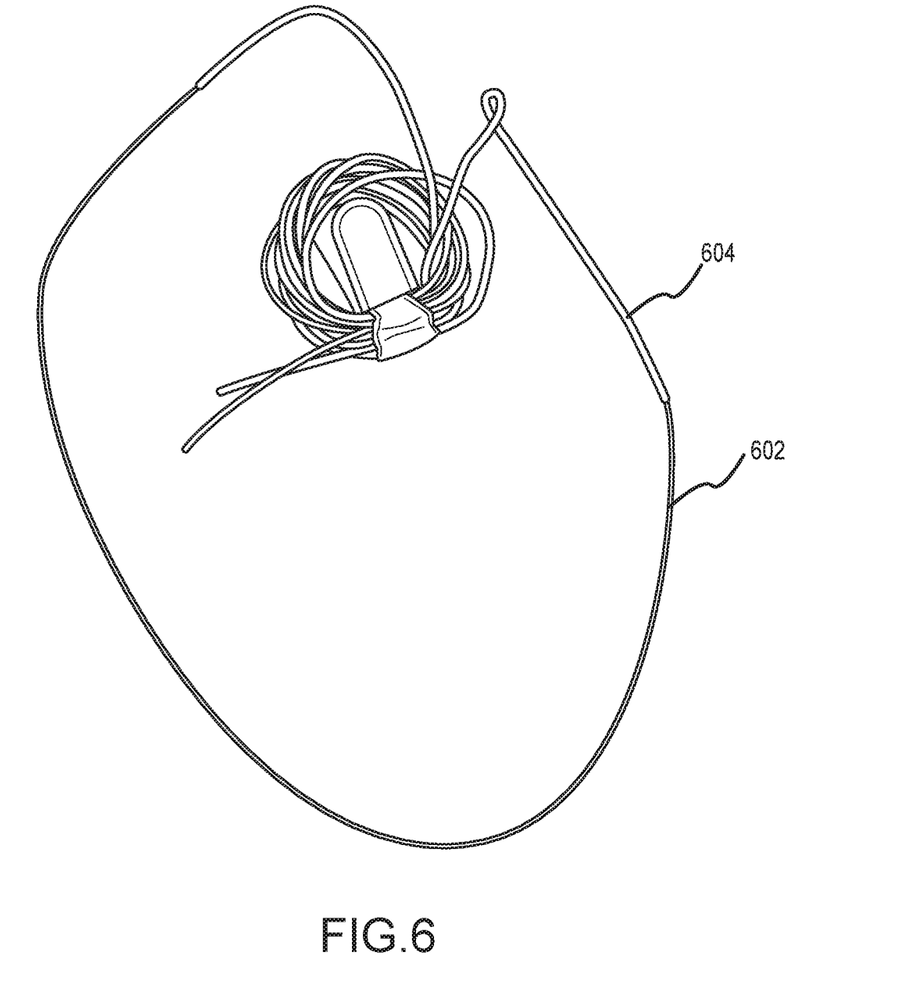
FIG. 6 is a photo of a thread according to embodiments of the present invention.

FIG. 6 is a photo of an example thread. Uncoiled portion 602 is fascia fiber, and coiled portion 604 is non-human-derived fiber. The fascia fiber is 12 to 18 inches long, and the non-human-derived fiber is 18 inches long. The non-human-derived fibers is Teleflex® Force Fiber® #2, which is a polyethylene fiber.

B. Example 2

Nine fascia fibers 12 to 18 inches long are obtained. The fascia fibers are tapered at both ends to reduce the diameter of the fiber at the end. Each of the fascia fibers are separately attached at one end to one end of a non-human-derived fiber of nylon, polyester, polyethylene, polygycolic acid, polylactic acid, polyvinylidene fluoride, polypropylene, catgut, or silk to form 9 separate threads. The non-human-derived fiber is about 18 inches long. The fascia fibers are attached to the non-human-derived fiber by cyanoacrylate adhesive. Each of the fascia fibers at the other end is then attached to the same type of non-human-derived fiber to form 9 separate threads with fascia fiber attached at both ends to separate non-human-derived fibers of the same type. The second non-human-derived fiber is about 18 inches long. The fascia fiber is attached to the second non-human-derived fiber by cyanoacrylate adhesive.

C. Example 3

Nine fascia fibers 12 to 18 inches long are obtained. One end of each fascia fibers is inserted into a separate tube about 1 inch in length. One end of a non-human-derived fiber of nylon, polyester, polyethylene, polygycolic acid, polylactic acid, polyvinylidene fluoride, polypropylene, catgut, and silk is each inserted into a separate tube. The separate tubes have an inner diameter slightly larger than the diameter of the fascia fiber and the non-human-derived fiber. The tube is heated to shrink the tube to bind the fascia fiber with the non-human-derived fiber. The non-human-derived fiber is about 18 inches long. The process of binding the fascia fiber with the non-human-derived fiber with a tube is repeated with the other end of the fascia fiber to a second non-human-derived fiber of the same type. The second non-human-derived fiber is about 18 inches long. Nine separate threads with fascia fiber attached at both ends to separate non-human-derived fibers of the same type are formed.

D. Example 4

Example 3 is repeated except that the fascia fibers are tapered at both ends before the fibers are inserted into the tube.

E. Example 5

Example 3 is repeated except that the fascia fibers are attached to the non-human-derived fibers with cyanoacrylate before shrinking the tube with applied heat.

F. Example 6

Example 4 is repeated except that the fascia fibers are attached to the non-human-derived fibers with cyanoacrylate before shrinking the tube with applied heat.

G. Example 7

Each of the threads of Examples 3, 4, 5, and 6 is attached to a surgical needle. Each thread is used for suturing. A knot is tied in each thread to close a wound or surgical incision in a patient. The non-human-derived fibers are then cut off the thread, leaving only fascia fiber in contact with the patient.

V. Embodiments

In a first aspect, embodiments may include a thread for suturing. The thread may include a first portion that includes a fascia fiber. The first portion may have a first end that includes the fascia fiber. The thread may also include a second portion that includes a non-human-derived fiber. The second portion may have a first end that includes the non-human-derived fiber. The first end of the second portion may be attached to the first end of the first portion.

In embodiments, the non-human-derived fiber may be a first non-human-derived fiber. The thread may further include a third portion that includes a second non-human-derived fiber. The first portion may have a second end that includes the fascia fiber. The third portion may have a first end that includes the second non-human-derived fiber. The first end of the third portion may be attached to the second end of the first portion. The first non-human-derived fiber and the second non-human-derived fiber may be the same type of fiber.

The thread may have a total length from 36 inches to 54 inches. The first portion may have a length from 12 inches to 18 inches. The second portion may have a length from 12 inches to 18 inches.

The first end of the second portion may be attached to the first end of the first portion by an adhesive. The adhesive may include a cyanoacrylate or a cyanoacrylate ester.

The thread may have a strength that allows the thread to be used as a surgical suture.

The first portion may have a diameter from 300 µm to 400 µm. The thread may have a maximum diameter that does not exceed the diameter of the first portion by greater than 50 µm.

In embodiments, the thread may further include a piercing element in contact with the second portion. The piercing element may be a surgical needle.

The fascia fiber may be obtained from a single cadaveric donor. The non-human-derived fiber may include nylon, polyester, polyethylene, polyglycolic acid, polylactic acid, polyvinylidene fluoride, polypropylene, catgut, or silk.

In a second aspect, embodiments may include methods of forming a thread. The methods may include attaching a first end of a fascia fiber to a first end of a first non-human-derived fiber. The methods may also include attaching a second end of the fascia fiber to a first end of a second non-human-derived fiber.

In embodiments, methods may include tapering the fascia fiber to form the first end of the fascia fiber before attaching the first end of the fascia fiber to the first end of the first non-human-derived fiber. Methods may also include tapering the fascia fiber to form the second end of the fascia fiber before attaching the second end of the fascia fiber to the first end of the second non-human-derived fiber.

In embodiments, attaching the first end of the fascia fiber to the first end of the first non-human-derived fiber may include applying an adhesive to at least one of the first end of the fascia fiber or the first end of the first non-human-derived fiber, and attaching the second end of the fascia fiber to the first end of the second non-human-derived fiber comprises applying the adhesive to at least one of the second end of the fascia fiber or the first end of the second non-human-derived fiber. The adhesive may include a cyanoacrylate or a cyanoacrylate ester.

In these and other embodiments, attaching the first end of the fascia fiber to the first end of the first non-human-derived fiber may include inserting the first end of the fascia fiber into a first end of a first tubular component, inserting the first end of the first non-human-derived fiber into a second end of the first tubular component, where the second end is on an opposite end of the first tubular component as the first end of the first tubular component, and reducing an inner diameter of the first tubular component.

In embodiments, attaching the second end of the fascia fiber to the first end of the second non-human-derived fiber may include inserting the second end of the fascia fiber into a first end of a second tubular component, inserting the first end of the second non-human-derived fiber into a second end of the second tubular component, where the second end is on an opposite end of the second tubular component as the first end of the second tubular component, and reducing an inner diameter of the second tubular component.

Reducing the inner diameter of the first tubular component may include heating the first tubular component. In some embodiments, reducing the inner diameter of the first tubular component comprises applying water to the first tubular component.

Methods may include forming the fascia fiber. The fascia fiber may be obtained from a single cadaveric donor.

Embodiments may include attaching a second end of the first non-human-derived fiber to a piercing element. In other embodiments, methods may include attaching a second end of the second non-human-derived fiber to a piercing element. The piercing element may be a surgical needle.

The first non-human-derived fiber and the second non-human-derived fiber may be the same type of fiber.

The thread may have a total length from 36 inches to 54 inches. The fascia fiber may have a length from 12 inches to 18 inches. The first non-human-derived fiber may have a length from 12 inches to 18 inches. The second non-human-derived fiber may have a length from 12 inches to 18 inches. The fascia fiber may have a diameter from 300 µm to 400 µm. The thread may have a maximum diameter that does not exceed the diameter of the fascia fiber by greater than 50 µm.

The first non-human-derived fiber or the second non-human-derived fiber may include nylon, polyester, polyethylene, polyglycolic acid, polylactic acid, polyvinylidene fluoride, polypropylene, catgut, or silk.

The thread formed may be any embodiment of a thread described herein.

In a third aspect, embodiments may include methods of suturing. The methods may include inserting a thread into a soft tissue. The thread may include a first portion that includes a fascia fiber and a second portion that includes a non-human-derived fiber. Inserting the thread into the soft tissue may include inserting the second portion into the soft tissue before the first portion. The methods may further include removing the second portion from the first portion when the first portion is in contact with the soft tissue.

In embodiments, the methods may include a thread that includes a third portion of a second non-human-derived fiber. The first portion may be attached to the second portion, and the first portion may be attached to the third portion. Inserting the thread into the soft tissue may not include inserting the third portion into the soft tissue. The methods may further include removing the third portion from the first portion when the first portion is in contact with the soft tissue. The soft tissue may be skin of a human patient.

In embodiments, the second portion of the thread may be in contact with a piercing element. Methods may also include inserting the piercing element into the soft tissue before inserting the thread into the soft tissue.

Methods may include fastening the first portion to the soft tissue. Embodiments may include tying the first portion to fasten the first portion to the soft tissue. Tying the first portion may include closing a wound or a surgical incision.

The soft tissue may not have an immunoresponse to the first portion. The thread may be any thread described herein.

All patents, patent publications, patent applications, journal articles, books, technical references, and the like discussed in the instant disclosure are incorporated herein by reference in their entirety for all purposes.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the tissue" includes reference to one or more tissues and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A thread for suturing, the thread comprising:
   a first portion comprising a fascia fiber, the first portion having a first end and a second end comprising the fascia fiber, the first portion extending from the first end to the second end;
   a second portion comprising a first non-human-derived fiber, the second portion having a first end comprising the first non-human-derived fiber, wherein:
      the first non-human-derived fiber comprises a synthetic fiber, catgut, or silk, and
      the first end of the second portion is attached to the first end of the first portion, and
   a third portion comprising a second non-human-derived fiber, the third portion having a first end comprising the second non-human-derived fiber, wherein:
      the second non-human-derived fiber comprises a synthetic fiber, catgut, or silk, and
      the first end of the third portion is attached to the second end of the first portion.

2. The thread of claim 1, wherein the first non-human-derived fiber and the second non-human-derived fiber are the same type of fiber.

3. The thread of claim 1, wherein the thread has a total length from 36 inches to 54 inches.

4. The thread of claim 1, wherein the first portion has a length from 12 inches to 18 inches.

5. The thread of claim 1, wherein the second portion has a length from 12 inches to 18 inches.

6. The thread of claim 1, wherein the first end of the second portion is attached to the first end of the first portion by an adhesive.

7. The thread of claim 6, wherein the adhesive comprises a cyanoacrylate or a cyanoacrylate ester.

8. The thread of claim 1, wherein the thread has a strength to withstand 5 lbs of force.

9. The thread of claim 1, wherein the first portion has a diameter from 300 µm to 400 µm.

10. The thread of claim 9, wherein the thread has a maximum diameter that does not exceed the diameter of the first portion by greater than 50 µm.

11. The thread of claim 1, wherein the fascia fiber is obtained from a single cadaveric donor.

12. The thread of claim 1, wherein the non-human-derived fiber comprises nylon, polyester, polyethylene, polyglycolic acid, polylactic acid, polyvinylidene fluoride, or polypropylene.

13. A method of forming a thread, the method comprising:
    attaching a first end of a fascia fiber to a first end of a first non-human-derived fiber, wherein the first non-human-derived fiber is a synthetic fiber, catgut, or silk; and
    attaching a second end of the fascia fiber to a first end of a second non-human-derived fiber, wherein the second non-human-derived fiber is a synthetic fiber, catgut, or silk.

14. The method of claim 13, further comprising:
    tapering the fascia fiber to form the first end of the fascia fiber before attaching the first end of the fascia fiber to the first end of the first non-human-derived fiber, and
    tapering the fascia fiber to form the second end of the fascia fiber before attaching the second end of the fascia fiber to the first end of the second non-human-derived fiber.

15. The method of claim 14, wherein:
    attaching the first end of the fascia fiber to the first end of the first non-human-derived fiber comprises applying an adhesive to at least one of the first end of the fascia fiber or the first end of the first non-human-derived fiber, and
    attaching the second end of the fascia fiber to the first end of the second non-human-derived fiber comprises applying the adhesive to at least one of the second end of the fascia fiber or the first end of the second non-human-derived fiber.

16. The method of claim 15, wherein the adhesive comprises a cyanoacrylate or a cyanoacrylate ester.

17. The method of claim 14, wherein:
    attaching the first end of the fascia fiber to the first end of the first non-human-derived fiber comprises:
       inserting the first end of the fascia fiber into a first end of a first tubular component,
       inserting the first end of the first non-human-derived fiber into a second end of the first tubular component, the second end on an opposite end of the first tubular component as the first end of the first tubular component, and
       reducing an inner diameter of the first tubular component.

18. The method of claim 17, wherein reducing the inner diameter of the first tubular component comprises heating the first tubular component.

19. The method of claim 17, wherein reducing the inner diameter of the first tubular component comprises applying water to the first tubular component.

20. The method of claim 14, wherein:
    attaching the second end of the fascia fiber to the first end of the second non-human-derived fiber comprises:
       inserting the second end of the fascia fiber into a first end of a second tubular component,
       inserting the first end of the second non-human-derived fiber into a second end of the second tubular component, the second end on an opposite end of the second tubular component as the first end of the second tubular component, and reducing an inner diameter of the second tubular component.

21. The method of claim 13, further comprising forming the fascia fiber.

22. The method of claim 13, wherein the fascia fiber is obtained from a single cadaveric donor.

23. The method of claim 13, wherein the first non-human-derived fiber and the second non-human-derived fiber are the same type of fiber.

24. The method of claim 13, wherein the first non-human-derived fiber comprises nylon, polyester, polyethylene, polyglycolic acid, polylactic acid, polyvinylidene fluoride, or polypropylene.

* * * * *